United States Patent

Mannheimer

[11] Patent Number: 5,842,982
[45] Date of Patent: Dec. 1, 1998

[54] INFANT NEONATAL PULSE OXIMETER SENSOR

[75] Inventor: Paul D. Mannheimer, Danville, Calif.

[73] Assignee: Nellcor Puritan Bennett Incorporated, Pleasanton, Calif.

[21] Appl. No.: 695,243

[22] Filed: Aug. 7, 1996

[51] Int. Cl.[6] ........................................................ A61B 5/00
[52] U.S. Cl. ........................... 600/340; 600/322; 600/344
[58] Field of Search ..................... 128/633, 664, 128/665; 600/310, 311, 315, 322, 323, 326, 340, 344, 473, 476

[56] References Cited

U.S. PATENT DOCUMENTS

| | | | |
|---|---|---|---|
| 1,741,340 | 12/1929 | Scholl . | |
| 5,125,403 | 6/1992 | Culp | 128/633 |
| 5,133,091 | 7/1992 | del Valle Mas | 2/239 |
| 5,170,786 | 12/1992 | Thomas et al. | 128/633 |
| 5,230,333 | 7/1993 | Yates et al. | 128/382 |
| 5,237,994 | 8/1993 | Goldberger | 128/633 |
| 5,337,744 | 8/1994 | Branigan | 128/633 |

FOREIGN PATENT DOCUMENTS 44 29 845 C 10/1995 Germany .
96/15714 5/1996 WIPO .

OTHER PUBLICATIONS

"Clinical Investigation—Evaluation of oxygen saturation monitoring by pulse oximetry in neonates in the delivery system", Ivan Dimich et al., Canadian Journal of Anaesthesia, 1991, pp. 985–988.

Primary Examiner—Jennifer Bahr
Assistant Examiner—Eric F. Winakur
Attorney, Agent, or Firm—Townsend and Townsend and Crew LLP

[57] ABSTRACT

An improved infant/neonatal pulse oximeter sensor substrate which is preferably conforming to the shape of the infant or neonate's foot. In one embodiment, the pad conforms to the heel of the infant, with the emitter and detector preferably being mounted in the region of the calcaneus bone. The heel pad can be held in place with a stretchable sock. In an alternate embodiment, the conformable pad is a sock with recesses or pockets cut in it for holding the emitter and detector.

30 Claims, 3 Drawing Sheets

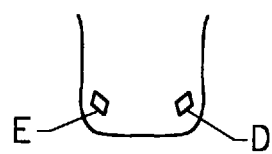 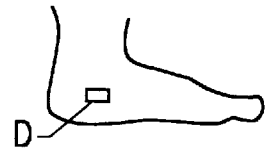
FIG. 8A             FIG. 8B
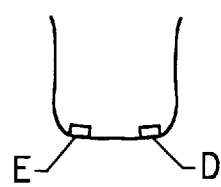 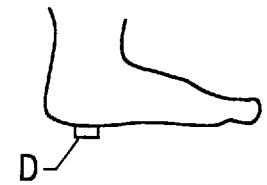
FIG. 9A             FIG. 9B
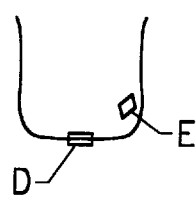 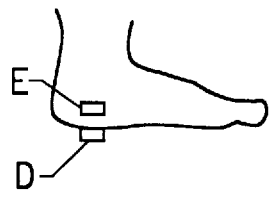
FIG. 10A            FIG. 10B
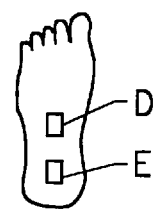 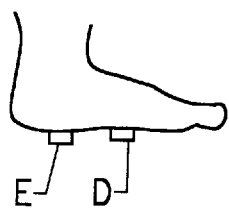
FIG. 11A            FIG. 11B

INFANT NEONATAL PULSE OXIMETER SENSOR

BACKGROUND OF THE INVENTION

The present invention relates to oximeter sensors, and in particular to pulse oximeter sensors for use on an infant's foot.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have typically been provided with a light source that is adapted to generate light of at least two different wavelengths, and with photodetectors sensitive to both of those wavelengths, in accordance with known techniques for measuring blood oxygen saturation.

Known non-invasive sensors include devices that are secured to a portion of the body, such as a finger, an ear or the scalp. In animals and humans, the tissue of these body portions is perfused with blood and the tissue surface is readily accessible to the sensor.

Pulse oximetry is used on infants and neonates in the NICU, and increasingly at home, for detection of hypoxemia. In the home, it is believed that early detection of hypoxic events may be a more reliable indicator and warning for the onset of Sudden Infant Death, and related disorders, than the currently used apnea monitors. Pulse oximetry sensors require attachment to the hand, foot, toe or finger (transmission sensors), or to a flat surface (reflectance sensors) where there is good perfusion of blood within the tissue. On small infants and neonates, the conventional approach is to tape the pulse oximetry sensor in place on the foot. For the home care market, this becomes an inconvenience as the sensor must be applied each and every time the baby is not being watched by the parents or other care provider. Repeatedly applying and removing the taped-on sensor is considered irritating to the skin of the baby, and leads to non-compliance by the parents. Additionally, adhesive sensors are generally single-use or limited re-use, adding a substantial expense to the cost of home monitoring. Clip-on sensors offer an alternative, but tend to fall off as well as being more motion sensitive.

A pulse oximeter sensor is typically applied across the top and bottom of the middle of an infant's foot. In one study, the pulse oximeter sensor was applied across the back of the foot above the heel at the achilles tendon ("Clinical Investigation, Evaluation of Oxygen Saturation Monitoring by Pulse Oximetry in Neonates in the Delivery System," Ivan Dimich et al., Canadian Journal of Anaesthesia, 1991, 38:8, pp 985–988).

SUMMARY OF THE INVENTION

The present invention provides an improved infant/neonatal pulse oximeter sensor which will attach to an infant's foot in an improved manner. Strong adhesives are not required, although a light adhesive or gel may be used to improve the conformance of the sensor of the invention. The invention preferably provides a pad which conforms or is conformable to the shape of the infant or neonate's foot, although a non-conforming pad or cup may also be used.

In one embodiment, the pad conforms to the heel of the infant, with the emitter and detector preferably being mounted below the achilles tendon and below the calcaneus bone. The heel pad can be held in place with a stretchable sock.

In an alternate embodiment, the conformable pad is a sock with pockets cut in it for holding the emitter and detector. A nylon mesh or other semi-transparent material forms the inside of the pockets, allowing light to escape the emitter and be detected by the detector.

Preferably, the cabling attached to the emitter and detector extends up the infant's heel a short distance to a connector which can be subsequently connected to a separate cable attached to a pulse oximeter monitor. The short cabling attached to the sensor provides more ease of attachment to an infant.

Additionally, the emitter and detector are preferably insertable into the pockets or depressions in the pad, thus making the emitter and detector reusable while the pad or sock can be disposable.

For a further understanding of the nature and advantages of the invention, reference should be made to the following description taken in conjunction with the accompanying drawings.

BRIEF DESCRIPTION OF THE DRAWINGS

FIGS. 8A–11B are diagrams illustrating different emitter and detector locations on a patient's heel.

DESCRIPTION OF THE PREFERRED EMBODIMENT

Figure 1:
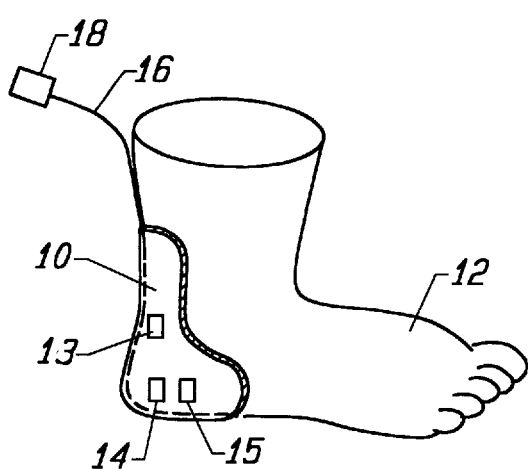
FIG. 1 is a diagram of one embodiment of heel pad sensor according to the present invention applied to an infant's foot.

FIG. 1 illustrates one embodiment of a sensor pad 10 attached to a foot 12 of an infant. Pad 10 conforms to the heel of the infant foot 12, and includes a light emitter 14 on one side, and a detector on the other side (not shown in FIG. 1). A cable 16 providing connections to the emitter and detector is connected to a connector 18. By keeping this cable short, the infant will not get wrapped up with it upon application of the pad, and it can be subsequently attached to another connector for a cable connected to a pulse oximeter monitor.

FIG. 1 also shows an optional ECG sensor 13, which would have a separate conductor in cable 16. In addition, an additional sensor 15 may be used, and may be a reflectance sensor. Additional sensor 15 may be a complete sensor, or just a detector which shares emitter 14. Alternately, a single detector could share two emitters. In such a reflectance sensor, the emitter and detector can be located on the side of the heel as shown in FIG. 1, or both components can be located on the bottom of the heel pad. Alternatively, one component may be on the side and one may be on the bottom.

Figure 2:
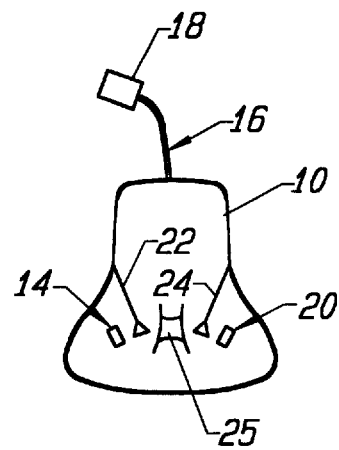
FIG. 2 is a diagram showing an inside view of the sensor of FIG. 1.

FIG. 2 illustrates pad 10 of FIG. 1 before application to the infant's foot. The view of FIG. 2 shows the inside of the heel pad cup. An emitter 14 and a detector 20 are shown. The emitter and detector can be separated sufficiently for a transmittance mode of operation, or can be placed closer together, or on the same side of the heel or on the bottom of the heel, for a reflectance mode of operation. The pad itself can be cut from flat material, which can be folded and glued along lines 22, 24, or molded to the proper shape. The pad could be made of a number of materials, such as foam, rubber or thermoplastic. Alternately, the pad may be constructed by laminating multiple layers together, sandwiching the optical components and wires internally. The pad is preferably held onto the heel by a stretchable sock, such as lycra or nylon, but may also be held in place with straps fabricated from a variety of materials such as Velcro. The sock should be of sufficient tightness to hold the heel pad to the heel without allowing it to move, but not so tight as to constrict blood flow.

FIG. 2 also shows a raised portion 25 which can serve as a shunt barrier. This will prevent light from shunting from the emitter to the detector without going through the infant's skin. The shunt barrier ridge 25 will abut up against the infant's heel even if the remainder does not, thus blocking a path for light around the end of the infant's heel.

Figure 3:
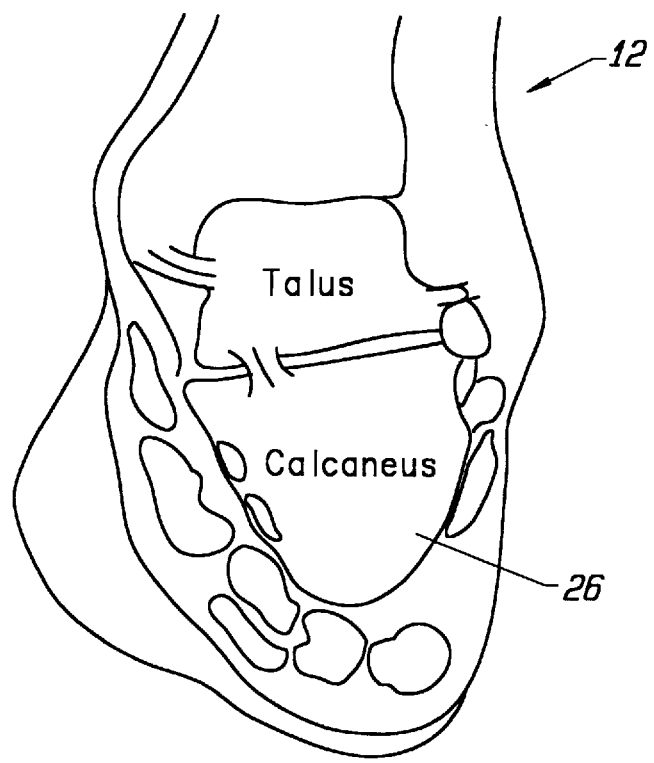
FIG. 3 is a diagram of an infant's foot showing the location of the calcaneus bone.

FIG. 3 shows a cutaway rear view of an infant's heel. Preferably, the emitter and detector are mounted below the calcaneus bone 26, as shown in FIG. 3. This region is well perfused with blood and allows sufficient light transmission for the oximeter to function properly.

An additional advantage of placing a sensor on the heel is that an infant's heel size changes little as it grows from a birth weight (approximately 7 pounds) up to around 22 pounds. By contrast, the bridge of the foot will increase size more dramatically.

The inventor also recognized that the heel provides a good registration position for a sensor, as opposed to other locations where it might be difficult to secure the sensor in the desired location. The use of a stretchable sock to hold the heel pad in place also can be advantageous in constricting the foot slightly, keeping venous blood out and thus reducing undesired artifacts in the detected signal and enhancing arterial pulse amplitude.

Figure 4:
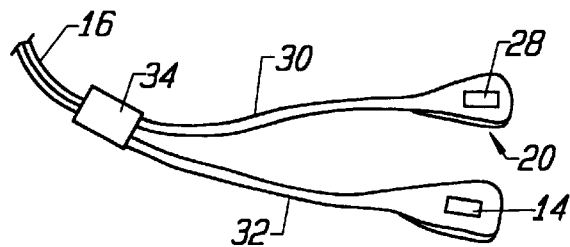
FIG. 4 is a diagram of a "Y-sensor" for use with a disposable pad for attaching to an infant's foot according to one embodiment of the invention.

In one embodiment, the heel pad is reusable, with openings in the pad for holding the emitter 14 and detector 20. FIG. 4 illustrates a "Y-sensor" having a separate emitter 14 and detector 20. These are mounted in plastic housings which have protrusions on the backside, with protrusion 28 being visible in the view shown. These protrusions can be inserted into correspondingly shaped recesses in the heel pad to secure the emitter and detector in place. The entire housing could also be placed in recesses having shapes conforming to those of the emitter and detector housings. Two cables 30 and 32 are joined by member 34, and thereafter a single cable assembly 16 is used. In this way, the separate portions don't extend very far, avoiding entanglement. Cables 30 and 32 can be fabricated from wires or by using flexible circuits.

Figure 5:
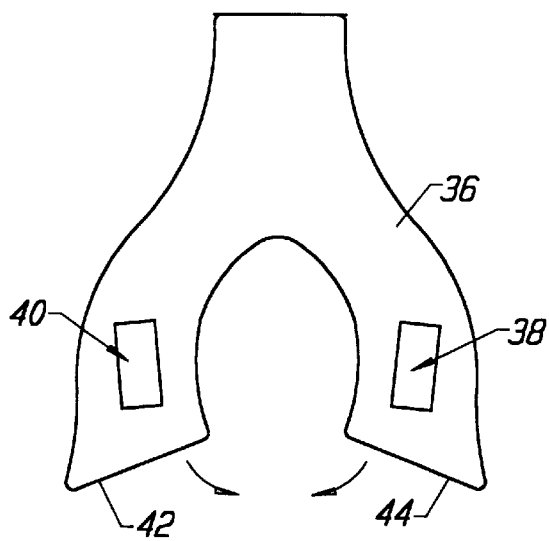
FIGS. 5 and 6 are disassembled and assembled diagrams, respectively, of one embodiment of a heel pad according to the present invention.
Figure 6:
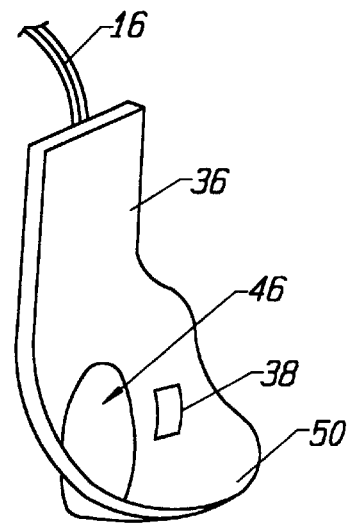

FIGS. 5 and 6 show an alternate embodiment of a heel pad. FIG. 5 illustrates a resilient material 36 with cutout windows 38 and 40 for the detector and emitter. Edges 42 and 44 can be glued together to form a heel cup as shown in FIG. 6. FIG. 6 shows the assembled heel cup pad 36 with cable 16 attached. In the assembled form, a rounded opening 46 provides for registration with the bottom of an infant's heel, and also allows the cup to accommodate heels of different size since different amounts of the heel will extend through the opening 46. Window 38 is shown in the view of FIG. 6, while window 40 is obscured. A front portion 50 of the pad is designed to slide slightly under the infant's heel when engaged.

Heel pad 36 could be made of a number of different materials, such as molded foam, rubber or thermoplastic. In particular, Neoprene™ rubber could be used, or a foam such Poron™ or Urethane™. Another possible material would be Santoprene™. Preferably, the material would have good memory, that is, it would retain its shape conformable to the foot even after being distorted by manipulation. Alternately, the heel pad may be constructed as a lamination of two or more layers of tapes, in a construction similar to the Nellcor N-25 Oxisensor. The heel pad may be conforming to the infant's foot, either as a hard, molded shape or as a pliable, conformable shape that can be distorted. Preferably, the heel pad is constructed with materials and configuration in such a manner so as to minimize optical interference from ambient light sources.

The emitter and detector can be flush in a recess in the heel pad, or alternately can be recessed to provide a specified air gap. The specified air gap could eliminate variations in the light path where, in response to motion, the emitter and detector are alternately in direct contact with the skin, and then have an air gap. By ensuring that there is always an air gap, the variations would be much less in the detected light due to motion. Alternately, the emitter and detector can be flush with the infant's foot.

Figure 7:
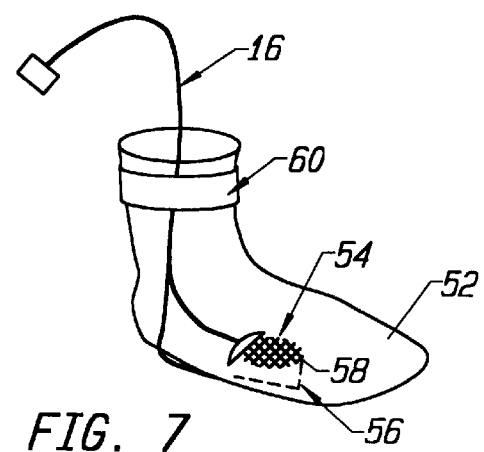
FIG. 7 is a diagram of an alternate embodiment of a sock-type pad according to the present invention.

FIG. 7 shows an alternate embodiment of the invention in which a special sock 52 is used having a pocket 54 on top of the foot, and a pocket 56 on the bottom of the foot. The emitter and detector can be inserted into the pockets and connected to cable 16. The inside of the pocket has a mesh 58 facing the infant's foot, which may be a nylon mesh, for instance. Alternatively, a transparent plastic or other material may be used. The mesh or transparent material must be sufficiently strong to hold the sensor in place in the pocket and sufficiently transparent to allow light to pass through it. An optional securing strap 60, such as a Velcro™ strap, is used to hold cable 16 in place, and prevent motion of the cable further away from the emitter and detector from moving the emitter and detector in the pockets. Pockets 56 and 58 could also be located across the heel pad below the Calcaneus as is practiced in FIG. 1. Alternately, a sock with recesses or holes for holding the emitter and detector could be used, without any covering between the emitter and detector and the patient's foot.

FIGS. 8–11 show alternate locations for the placement of an emitter and detector according to the present invention. FIG. 8A is a bottom view, and FIG. 8B is a side view, illustrating the emitter and detector being on the side of a foot adjacent a heel of a patient. FIGS. 9A and 9B illustrate bottom and side views, respectively, of the emitter and detector being adjacent each other along the bottom of the heel, aligned side-by-side. FIGS. 11A and 11B illustrate a view of the emitter and detector aligned along the bottom of a heel on a line extending from the front to back of a foot. FIGS. 10A and 10B illustrate the detector being on the bottom of the heel, while the emitter is on the side. Alternately, these positions can be reversed, or any other combination of the positions set forth in FIGS. 8–11 could be used.

As will be understood by those of skill in the art, the present invention may be embodied in other specific forms without departing from the spirit or essential characteristics thereof. Constituents other than arterial blood oxygen saturation may be determined, such as glucose, blood gases, or blood flow characteristics. Furthermore, optical fibers or optical fiber bundles may be used to couple one or both the light source and light detector to the substrate, with the electro-optic emitter and/or detection placed in a remote location. Accordingly, the foregoing description is intended to be illustrative, but not limiting, of the scope of the invention which is set forth in the following claims.

What is claimed is:

1. An optical method for determination of a blood characteristic comprising the steps of:
   applying an emitter and detector to spaced-apart positions on a heel of a patient in the region of the calcaneus bone;
   securing said emitter and detector to said patient;
   emitting electromagnetic radiation with said emitter;
   detecting electromagnetic radiation scattered by said heel with said detector and producing a detector signal; and
   determining a blood characteristic in said patient from said detector signal.

2. The method of claim 1 further comprising the step of detecting transmitted light with said detector.

3. The method of claim 1 further comprising the step of detecting reflected light with said detector.

4. The method of claim 1 wherein said blood characteristic is oxygen saturation.

5. The method of claim 1 wherein said steps are applied to a patient weighing less than 15 kg.

6. An optical method for determination of a blood characteristic comprising the steps of:
   applying an emitter and detector to spaced-apart positions on a heel of a patient in the region of the calcaneus bone;
   securing said emitter and detector to said patient by placing a sock over said emitter and detector:
   emitting electromagnetic radiation with said emitter;
   detecting electromagnetic radiation scattered by said heel with said detector and producing a detector signal; and
   determining a blood characteristic in said patient from said detector signal.

7. An optical method for determination of a blood characteristic comprising the steps of:
   applying an emitter and detector to spaced-apart positions on a heel of a patient in the region of the calcaneus bone;
   securing said emitter and detector to said patient by attaching said emitter and detector to a sock:
   emitting electromagnetic radiation with said emitter;
   detecting electromagnetic radiation scattered by said heel with said detector and producing a detector signal; and
   determining a blood characteristic in said patient from said detector signal.

8. An oximeter sensor comprising:
   a non-adhesive substrate, having a shape similar to a shape of at least a portion of a patient's foot and including a section adapted to substantially envelop a heel of the patient's foot;
   an emitter coupled to said substrate at a position located on said section; and
   a detector coupled to said substrate a distance from said emitter.

9. The sensor of claim 8 further comprising at least one strap for holding said substrate against said patient's foot.

10. The sensor of claim 8 wherein said substrate comprises a plurality of laminated layers.

11. The sensor of claim 8 wherein at least one of said emitter and detector is on one of a side, bottom and rear of said foot.

12. The sensor of claim 8 wherein at least one of said emitter and detector is recessed in said substrate to form an air gap between said one of said emitter and detector and said foot.

13. The oximeter sensor of claim 8 wherein said substrate is resilient and has a shape conformable to a heel of a patient.

14. The oximeter sensor of claim 13 wherein said emitter and detector are mounted in said resilient substrate to engage an infant patient's heel below the calcaneus bone.

15. The oximeter sensor of claim 13 further comprising leads connected to said emitter and said detector, said leads extending upward along said substrate away from the bottom of a patient's foot.

16. The oximeter sensor of claim 13 wherein said emitter and detector are mounted on opposite sides of said patient's foot for transmittance oximetry.

17. The oximeter sensor of claim 8 wherein said emitter and said detector are removably mounted in said substrate.

18. The oximeter sensor of claim 8 wherein said sensor is a pulse oximeter sensor.

19. The oximeter sensor of claim 8 further comprising a second detector mounted in said substrate.

20. An oximeter sensor comprising:
    a non-adhesive substrate, having a shape similar to a shape of at least a portion of a patient's foot;
    an emitter coupled to said substrate;
    a detector coupled to said substrate a distance from said emitter; and
    a sock for holding said substrate against said patient's foot.

21. An oximeter sensor comprising:
    a non-adhesive substrate, having a shape similar to a shape of at least a portion of a patient's foot;
    an emitter coupled to said substrate;
    a detector coupled to said substrate a distance from said emitter; and
    wherein said substrate comprises a sock, said sock including:
      a first pocket for securing said emitter, said first pocket including a substantially transparent material between said emitter and said patient; and
      a second pocket for securing said detector, said second pocket including a substantially transparent material between said emitter and detector.

22. An oximeter sensor comprising:
    a non-adhesive substrate, having a shape similar to a shape of at least a portion of a patient's foot;
    an emitter coupled to said substrate;
    a detector coupled to said substrate a distance from said emitter;
    wherein said substrate comprises a sock, said sock including cavities for holding said emitter and said detector.

23. An oximeter sensor comprising:

a non-adhesive substrate, having a shape similar to a shape of at least a portion of a patient's foot;

an emitter coupled to said substrate;

a detector coupled to said substrate a distance from said emitter; and an ECG sensor mounted in said substrate.

24. An oximeter sensor housing comprising:

a substrate, having a shape similar to a shape of a patient's heel and including a section adapted to substantially envelop said patient's heel;

a first cavity in said substrate at a position located on said section having a shape to support an oximeter emitter; and a second cavity in said substrate a distance from said first cavity a having a shape to support an oximeter detector.

25. The oximeter sensor housing of claim 24 wherein said substrate further comprises a bottom portion for engaging a bottom of said patient's heel and a gap above said bottom portion for allowing a portion of said patient's heel to extend into said gap.

26. The oximeter sensor housing of claim 24 wherein said substrate is resilient.

27. The oximeter sensor housing of claim 24 further comprising:

leads having first ends connected adjacent said first and second cavities; and a connector coupled to second ends of said leads.

28. An oximeter sensor housing comprising:

a substrate, having a shape similar to a shape of a patient's heel;

a first cavity in said substrate having a shape to support an oximeter emitter;

a second cavity in said substrate a distance from said first cavity having a shape to support an oximeter detector; and a shunt barrier between said first and second cavities;

wherein said substrate further comprises a bottom portion for engaging a bottom of said patient's heel and a gap above said bottom portion for allowing a portion of said patient's heel to extend into said gap.

29. The oximeter sensor housing of claim 28 wherein said shunt barrier comprises a ridge in said substrate extending inward to engage with said heel.

30. The oximeter sensor housing of claim 27 wherein said leads are less than one foot long.

* * * * *